(12) United States Patent
Rose et al.

(10) Patent No.: US 7,197,111 B2
(45) Date of Patent: Mar. 27, 2007

(54) PROCESS AND APPARATUS FOR IRRADIATING PRODUCT PALLETS

(75) Inventors: Graham Rose, Nepean (CA); Muriel Vander Donckt, Brussels (BE); Frédéric Stichelbaut, Walhain (BE); Olivier Gregoire, Louvain-la-Neuve (BE)

(73) Assignee: Ion Beam Applications S.A. (BE)

( * ) Notice: Subject to any disclaimer, the term of this patent is extended or adjusted under 35 U.S.C. 154(b) by 0 days.

(21) Appl. No.: 10/491,563

(22) PCT Filed: Dec. 3, 2001

(86) PCT No.: PCT/BE01/00204

§ 371 (c)(1),
(2), (4) Date: Oct. 29, 2004

(87) PCT Pub. No.: WO03/028771

PCT Pub. Date: Apr. 10, 2003

(65) Prior Publication Data

US 2005/0058246 A1  Mar. 17, 2005

(30) Foreign Application Priority Data

Oct. 4, 2001  (EP) .................................. 01870212

(51) Int. Cl.
*G01N 23/04* (2006.01)

(52) U.S. Cl. ......................................... 378/57; 378/69

(58) Field of Classification Search .................. 378/57, 378/55, 68–69, 208; 198/347.1, 349.3; 250/559.06, 250/454.11, 453.11, 223 R, 492.23, 492.4
See application file for complete search history.

(56) References Cited

U.S. PATENT DOCUMENTS 4,018,348 A   4/1977   Bosshard (Continued)

FOREIGN PATENT DOCUMENTS

DE        217 349        1/1985

(Continued)

*Primary Examiner*—Edward J. Glick
*Assistant Examiner*—Hoon Song
(74) *Attorney, Agent, or Firm*—Fitch, Even, Tabin & Flannery

(57) ABSTRACT

The present invention is related to a process for irradiation of a product pallet having four vertical faces by a photon beam such as an X-ray beam, a gamma source or similar, consisting in an irradiation procedure comprising the following steps:
introducing the product pallet into an irradiation zone according to a horizontal translation movement,
submitting said product pallet to said photon beam, the source of which having a vertical movement, the horizontal translation movement of the product pallet and the vertical movement of the beam resulting in the irradiation of a vertical face of said product pallet,
moving out said product pallet from the irradiation zone.
giving a rotation of substantially 90° to said product pallet using rotation means,
repeating said irradiation process until at least the four vertical faces of said product pallet have been irradiated.

The present invention is also related to an apparatus and to the use of said process or said apparatus for irradiating a product arranged on a pallet, said product being either of low or of high density.

28 Claims, 7 Drawing Sheets

U.S. PATENT DOCUMENTS

| | | | |
|---|---|---|---|
| 4,066,907 A | 1/1978 | Tetzlaff | |
| 5,001,352 A | 3/1991 | Tetzlaff | |
| 5,396,074 A * | 3/1995 | Peck et al. | 250/454.11 |
| 6,215,847 B1 | 4/2001 | Perrins et al. | |
| 6,285,030 B1 * | 9/2001 | Williams et al. | 250/454.11 |
| 6,504,898 B1 * | 1/2003 | Kotler et al. | 378/64 |

FOREIGN PATENT DOCUMENTS

| | | |
|---|---|---|
| EP | 0 999 556 | 5/2000 |
| GB | 1 206 151 | 9/1970 |
| JP | 8-220299 | 8/1996 |

* cited by examiner

PROCESS AND APPARATUS FOR IRRADIATING PRODUCT PALLETS

FIELD OF THE INVENTION

The present invention is related to a process and an apparatus for irradiating products conveyed on pallets with high energy radiation beam.

A possible application of such process and apparatus is the sterilisation of products.

STATE OF THE ART

Irradiation systems are used nowadays to sterilise a great variety of products such as medical devices, food, food utensils or cosmetics by means of a high energy ionising radiation source, for example gamma radiation, X-rays or an electron beam.

Typically, in these irradiation systems, products are loaded either on pallets or on unique carrier trays and maintained in a store before the irradiation chamber before being conveyed past the radiation source for irradiation. A second pass of the pallets or carriers is then planned in order to expose their other side to the radiation source. The pallets or carriers are finally diverted to an unloading area.

To be efficient, the irradiation system has to provide an even exposure of the product. It is generally admitted that this condition is satisfied if the dose-uniformity ratio also known as "DUR", corresponding to the ratio between the maximum dose and the minimum dose, is as low as possible and approaches 1.

Different technical solutions have been proposed in the prior art in order to have a uniform irradiation of the product. Examples are given by documents U.S. Pat. Nos. 4,066,907 and 4,018,348 wherein turntables are coupled with conveyor systems to expose product to the radiation source. The product handling with the device disclosed in these documents is unfortunately very time-consuming as it requires unpacking and repackaging of the product from a pallet to a carrier.

This problem also exists for the irradiation system disclosed in document U.S. Pat. No. 5,396,074, wherein an overhead transport conveyor is used to suspend article carriers and bring them in front of the radiation source, said carriers being able to rotate upon their vertical axes so that both sides of the carriers can be irradiated. Moreover, this irradiation system is limited to the treatment of low density products, due to the problem of radiation penetration depth in the product possibly associated with the electron beam comprised therein.

Indeed, the density of the product to be irradiated is a critical parameter to take into account in order to have an efficient irradiation. The radiation source has thus to be sufficiently energetic so as to penetrate in the core of the product. In practice, the minimum dose delivered by the irradiation system has to be greater than 2 kGy for products like foodstuffs but greater than 25 kGy for products like medical devices. With this aim also, the configuration (orientation) of the product when it passes in front of the radiation source has to be optimised.

AIMS OF THE INVENTION

The present invention aims to provide a process and an apparatus for irradiating products, which do not present the drawbacks of the processes and devices of the state of the art mentioned here above.

More precisely, the present invention aims to provide a process and an apparatus, which allow to irradiate a great variety of products which can be as different as medical devices and foodstuffs.

Another aim of the present invention is to provide a process and an apparatus, which allow a uniform irradiation of low density products (densities 0.2 g/cm$^3$) as well as of high density products (densities >0.2 g/cm$^3$).

The present invention also aims to provide a process and an apparatus for performing secured and reliable irradiations with moderate cost in terms of equipment as well as in terms of treatment time.

In particular, the present invention aims to provide a process and an apparatus, which allow simultaneous irradiation of a great quantity of products maintained on pallets.

SUMMARY OF THE INVENTION

The present invention is related to a process for irradiation of a product pallet having four vertical faces by a photon beam such as an X-ray beam, a gamma source or similar, said process comprising the following steps:

introducing the product pallet into an irradiation zone according to a horizontal translation movement, submitting said product pallet to said photon beam having a vertical movement, the horizontal translation movement of the product pallet and the vertical movement of the beam resulting in the irradiation of a vertical face of said product pallet, moving out said product pallet from the irradiation zone, giving a rotation of substantially 90° to said product pallet using rotation means, said irradiation process being reproduced until at least the four vertical faces of said product pallet have been irradiated.

Advantageously, in said process, the rotation of the product pallet is performed outside the irradiation zone.

Preferably, the horizontal and/or vertical spread of the photon beam is limited.

The present invention is also related to a process for irradiation of a product pallet having four vertical faces by a photon beam such as an X-ray beam, a gamma source or similar, said process comprising the following steps:

introducing the product pallet into an irradiation zone according to a horizontal translation movement, submitting said product pallet to said photon beam, the source of which having a vertical movement, the horizontal translation movement of the product pallet and the vertical movement of the beam resulting in the irradiation of a vertical face of said product pallet, moving out said product pallet from the irradiation zone, wherein the horizontal and/or vertical spread of the photon beam is limited.

Preferably, said process further comprises the step of giving a rotation of substantially 90° to said product pallet using rotation means, said irradiation process being reproduced until at least the four vertical of said product pallet have been irradiated.

Preferably, the rotation of the product pallet is performed outside the irradiation zone.

Advantageously, the product pallet is transferred in front of the photon beam in the irradiation zone according to a horizontal translation movement.

In a preferred embodiment, the speed of the product pallet according to the horizontal translation movement is varied or modulated.

Preferably, the horizontal translation speed of the product pallet is lower when the centre of the product pallet is in front of the photon beam.

The speed of the vertical movement of the photon source may also be modulated.

Preferably, the speed of the vertical movement of the photon source is lower when the centre of the product pallet is in front of the photon beam.

The speed of the vertical movement of the photon source may be performed by scanning elements.

According to another embodiment, the intensity of the photon beam is modulated.

The product pallet may possibly consist in a first and a second product pallets, the second product pallet being under the first product pallet during a first irradiation process and the first product pallet being under the second product pallet during a further irradiation process.

Advantageously, the total height of the product and the pallet is measured prior to irradiation in order to adapt the vertical scanning function.

Advantageously also, the spread of the photon beam is adapted so as to allow an overscan of the product.

Preferably, the scanning photon beam has an asymmetric width covering a longer area below the product than above.

In a preferred embodiment, the irradiation of the product pallets is performed by batches of pallets loaded with products of similar densities.

In the process according to the present invention, the rotation means preferably consist in a turntable or in a curved conveyor part defining a 90° turn.

The present invention is also related to an apparatus for irradiating a product pallet having four vertical faces by a photon beam such as a X-ray beam, a gamma source, having
1) A photon beam source,
2) Means for conveying said product pallet into and out of the irradiation zone,
3) Means for translating said pallet inside the irradiation zone in front of the photon beam,
4) Scanning means in order to involve a vertical movement to said photon source,
5) Means for rotating the product pallet at an angle of substantially 90°.

Preferably, said apparatus further comprises homogenisation means such as collimators in order to limit the horizontal and/or vertical spread of the photon beam.

Furthermore, the present invention pertains to an apparatus for irradiating a product pallet having four vertical faces by a photon beam such as a X-ray beam, a gamma source, having
1) A photon beam source,
2) Means for conveying said product pallet into and out of the irradiation zone,
3) Means for translating said pallet inside the irradiation zone in front of the photon beam,
4) Scanning means in order to involve a vertical movement to said photon source,
5) Homogenisation means such as collimators in order in limit the horizontal and/or vertical spread of the photon beam.

Preferably, said apparatus further comprises means for rotating the product pallet at an angle of substantially 90°.

Preferably, the apparatus according to the present invention further comprises means for modulating the horizontal translation speed of the conveying means of the product pallet in front of the photon beam.

Preferably, the apparatus according to the present invention further comprises means for modulating the vertical translation speed of the scanning means of the photon source.

The means for rotating the product pallet may consist in a turntable.

They may also consist in a curved conveyor part defining a 90° turn.

The present invention is also related to the use of the processes or the apparatus mentioned hereabove for irradiating product pallets, said products being either of low density or high density.

SHORT DESCRIPTION OF THE DRAWINGS

FIG. 1a represents a general top view of the irradiation apparatus according to one embodiment of the present invention.

FIG. 1b corresponds a detailed view of FIG. 1a wherein the turntable according to the present invention is represented.

Figures 5A, 5B, 5C:
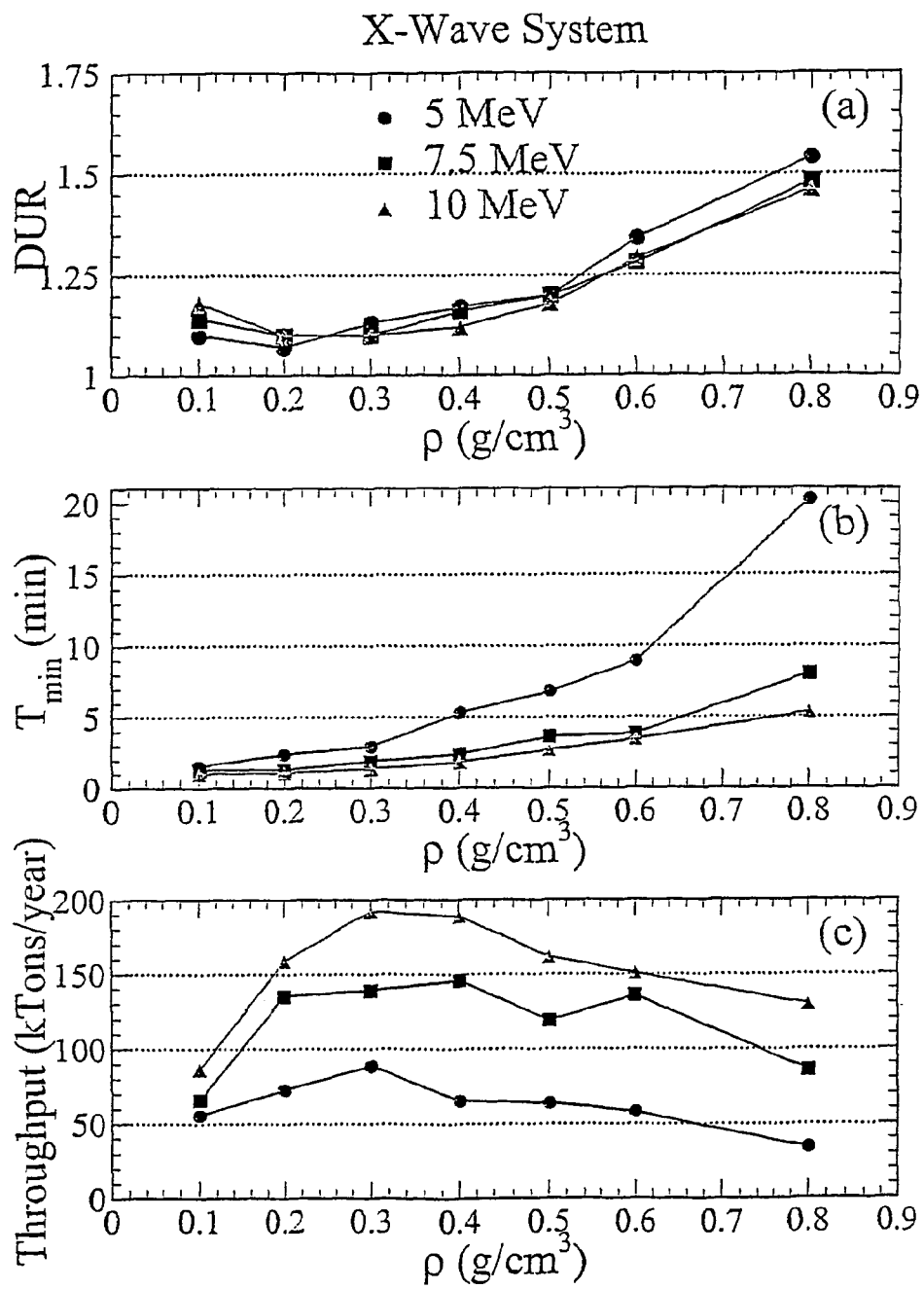
FIG. 5a–5c illustrate the performances of the apparatus according to the present invention as estimated by Monte-Carlo simulation techniques for electron beam energies of 5 MeV, 7.5 MeV and 10 MeV.

More precisely, FIG. 5a gives the dose uniformity ratio (DUR) evolution as a function of the density $\rho$ (g/cm$^3$) of the product on the pallet.

FIG. 5b gives the evolution of the pallet irradiation time as a function of the product density $\rho$ (g/cm$^3$) on the pallet.

FIG. 5c gives the treatment capacity per year as a function of the product density $\rho$ (g/cm$^3$) on the pallet.

DESCRIPTION OF A PREFERRED
EMBODIMENT OF THE INVENTION

A preferred embodiment of the present invention is illustrated on FIG. 1.

The apparatus comprises an irradiation chamber 1 where irradiation takes place and a classical conveyor system 2 to bring pallets supporting the products in front of the radiation source 4 in said irradiation chamber 1. The circuit of the conveyor system 2 is divided in five portions.

The first portion corresponds to a loading part 5 along which pallets to be irradiated are transported in the direction of radiation source 4.

The second portion corresponds to an accumulation area 6 where pallets are maintained in a queue before being exposed to the radiation source 4.

The third portion of the conveyor circuit is the exposure portion 7 located in front of the radiation source 4 where products are irradiated pallet by pallet.

The fourth portion is the check portion 8 where irradiated pallets are checked by the control unit of the irradiation apparatus. Appropriate detection means located on the pallets allow the control unit of the irradiation apparatus to test whether the irradiation of the pallets has been performed and to orientate them in the circuit.

Figure 1A:
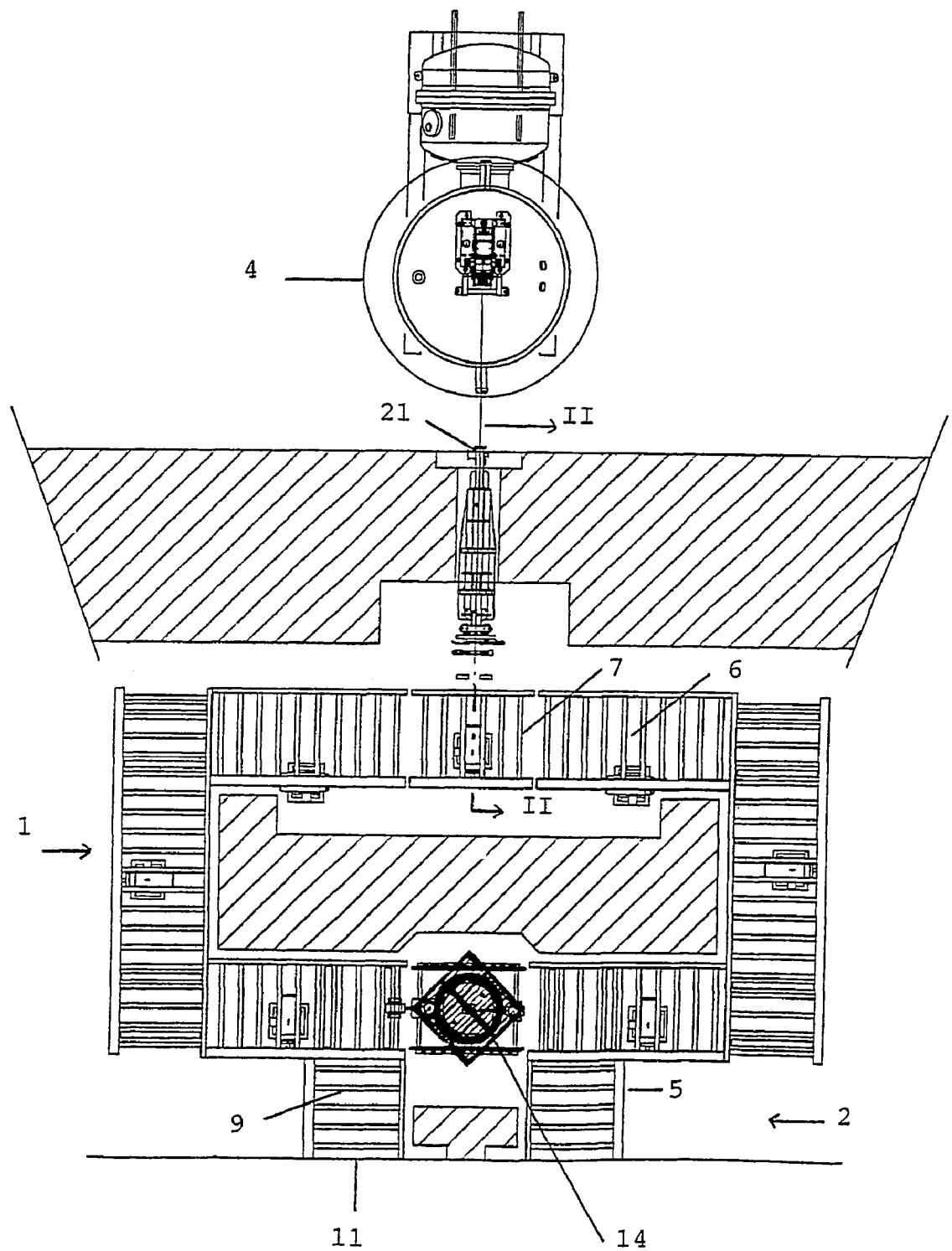
FIG. 1c represents a general top view of the irradiation apparatus according to another embodiment of the present invention.

More precisely, if the pallets have been sufficiently irradiated according to specific predetermined requirements, they are driven onto a fifth portion of the circuit corresponding to an unloading portion 9 along which pallets go out of the irradiation chamber 1 (through exit 11) and are unloaded. If the pallets have been insufficiently irradiated, they are transferred into a sixth portion which is the reorientation portion 10 where pallets are reoriented by a 90° rotation along their vertical axis using rotation means 14 and then transferred to the accumulation portion 6 for another pass in front of the radiation source 4. The rotation of the pallets takes thus place far away from the exposure portion 7. The rotation means can be a turntable as illustrated in FIG. 1*a*, but any other rotation means can also be suitable. For example, the rotation means may consist in a curved conveyor section arranged defining a 90 degrees turn 14' as shown on FIG. 1*c* (compare with the corresponding corner on FIG. 1*a*).

Figure 1B:
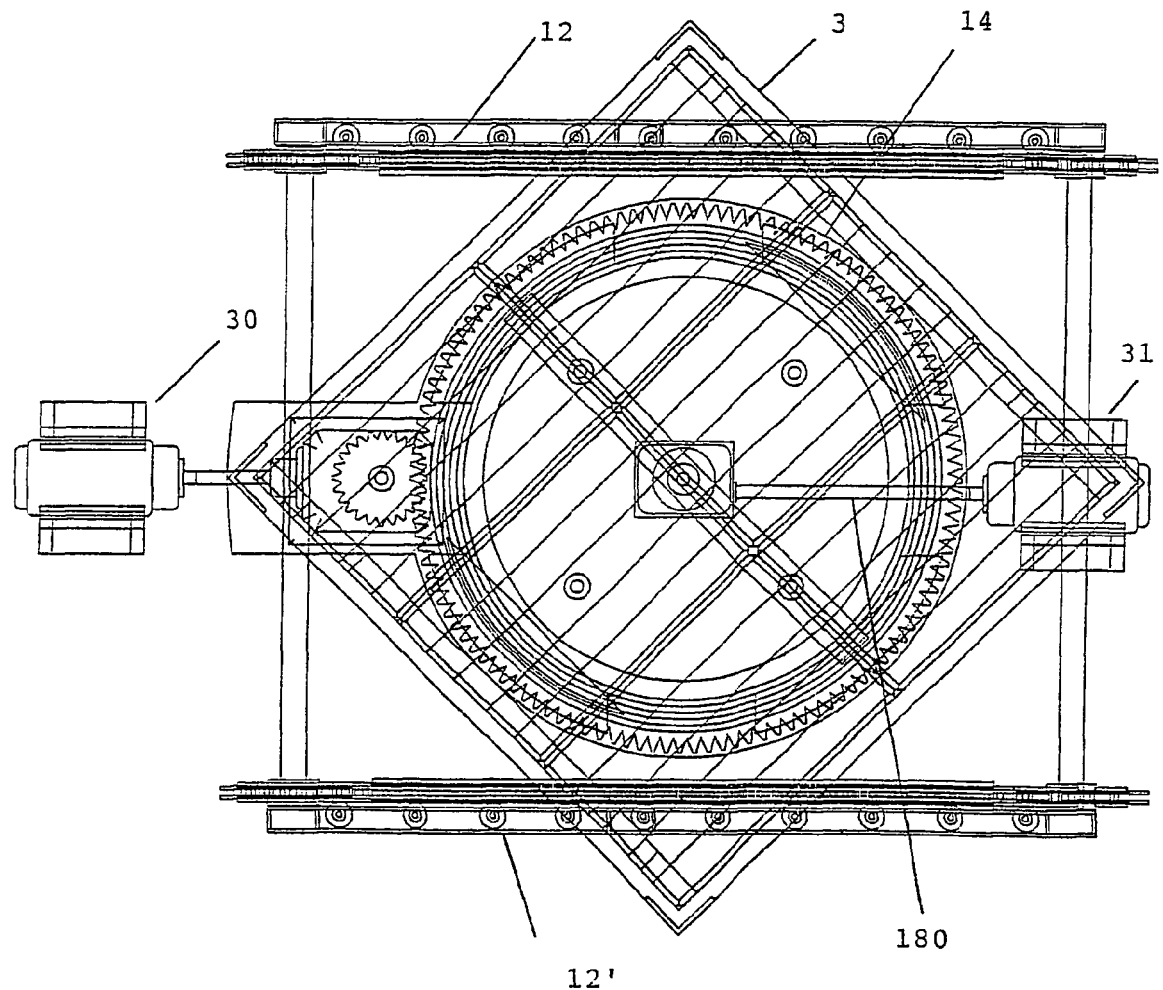
Figure 1C:
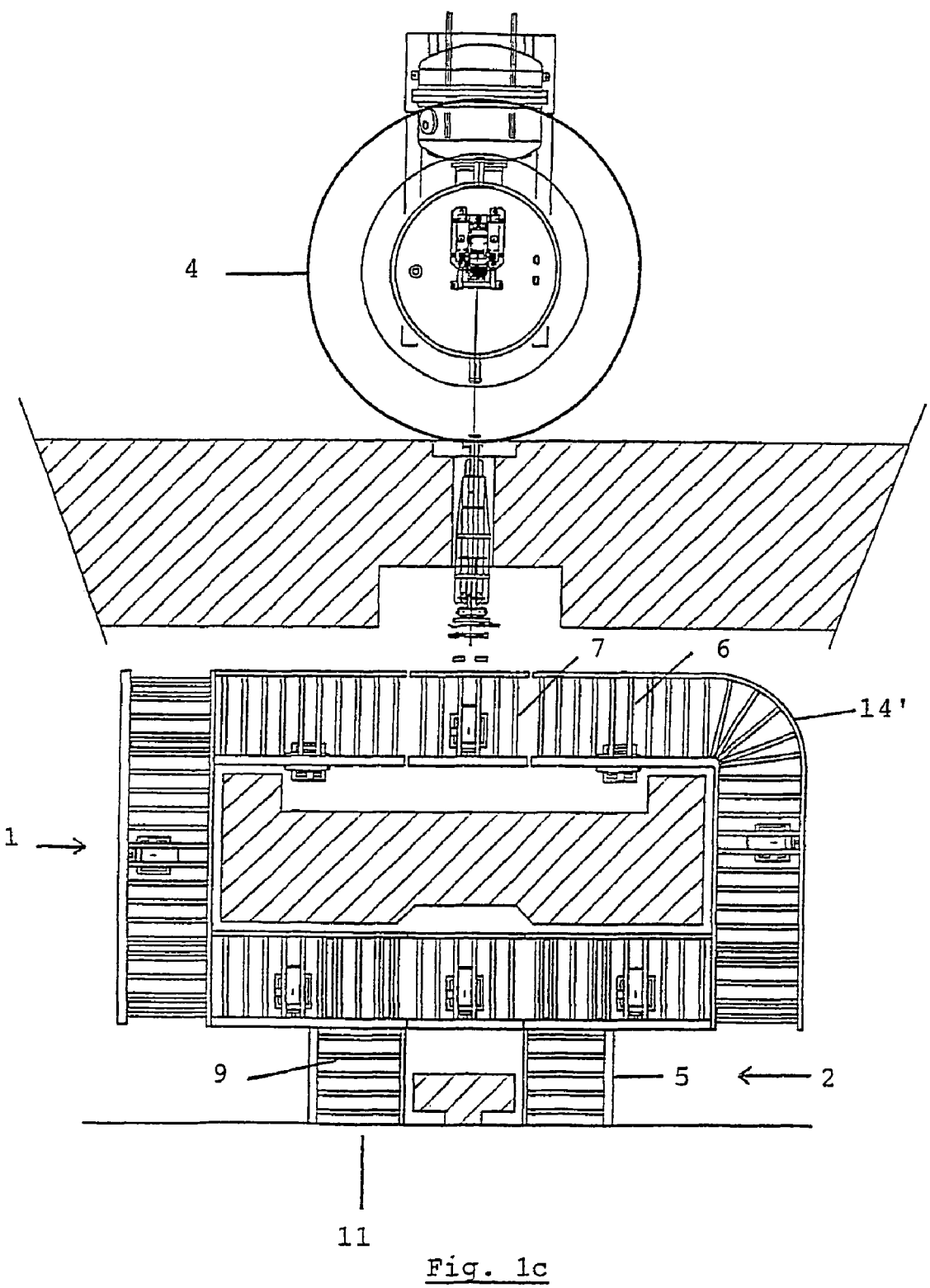

Practically, the rotation of a pallet is carried out by the turntable 14 as represented in FIGS. 1*a* and 1*b* according to the following steps. Initially, the product pallet 3 arrives in the reorientation portion supported on chains 12,12' above the turntable 14. A pneumatic jack 180 under the control of control means 31 lifts the turntable 14 up to the product pallet 3, so as to load the product pallet 3 on the turntable 14. Then the control means 30 operate a 90° rotation of the turntable 14 loaded with the product pallet 3. Once the pallet has been reoriented, the pneumatic jack 180 lowers the turntable 14 down on the chains 12,12'. The reoriented pallet 3 is then forwarded by conveyor means for further processing.

Preferably, the specific requirements concerning the irradiation are predetermined so that four passes of the pallets 3 in front of the radiation source 4 are planned (four-sides exposure).

Figure 2:
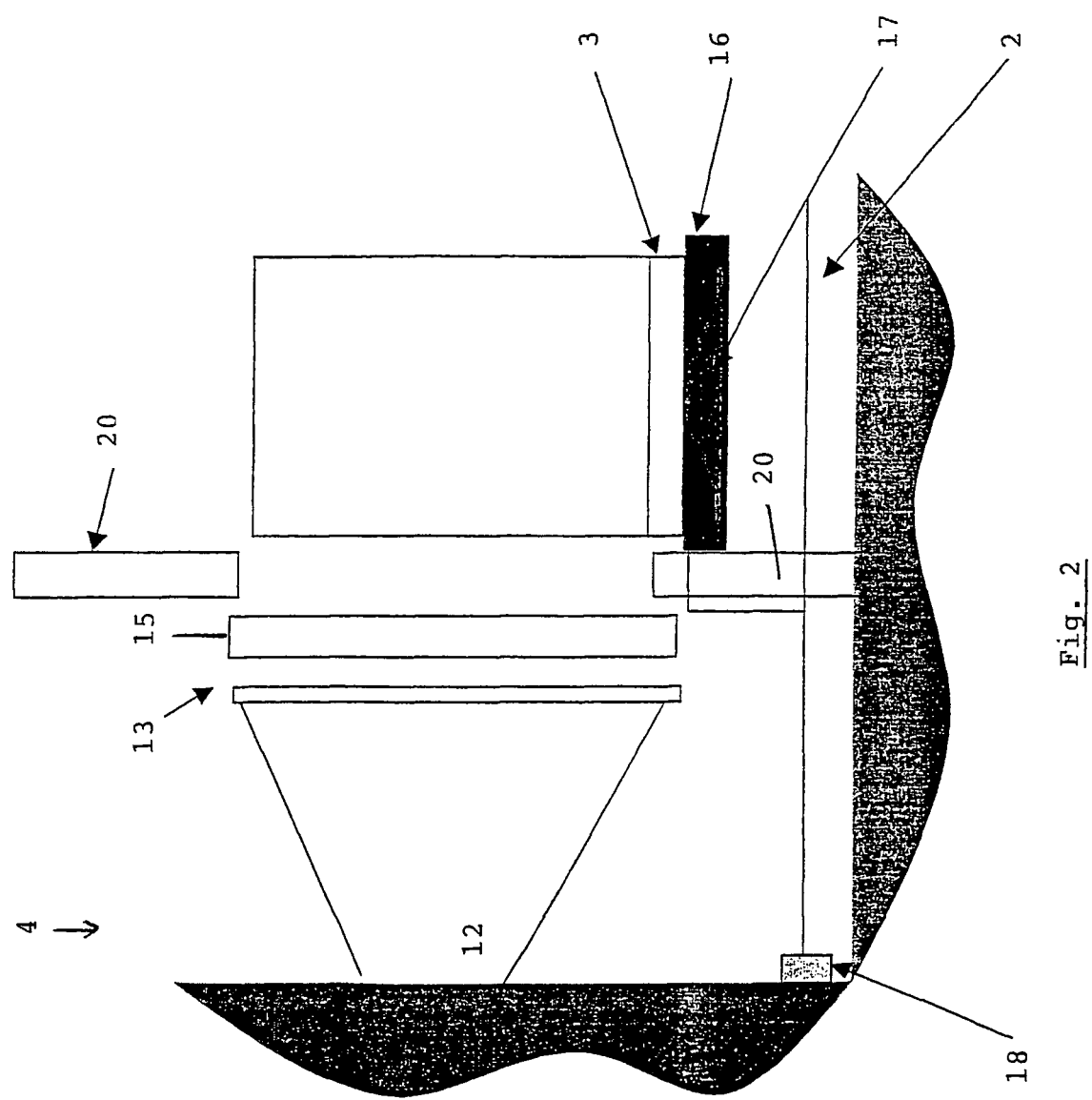
FIG. 2 represents a vertical sectional view along the line II—II of FIG. 1a, showing the relative arrangement of the electron beam horn, the X-ray target and the pallet to be irradiated.

As illustrated on FIG. 2, the radiation source 4 preferably comprises an electron beam source 12 (e-beam horn) which irradiates an X-ray target 13 which generates an X-ray beam (photon beam) for pallet irradiation.

Advantageously, the movement of the pallets 3 along the conveyor, and in particular in front of the radiation source, corresponds to a horizontal translation movement and the pallets are vertically scanned by the photon beam.

The pallets 3 used herein are standard pallets, typically 100×120×180 cm³ (depth/width/height). Said pallets are kept along the conveyor system 2 as close as possible to each other in order to achieve high throughput and to maximise the dose uniformity between the centre of the pallets 3 and their sides.

As illustrated on FIG. 2, a slave pallet 16 is arranged below each pallet 3 in order to position with a high precision the pallet 3 on the conveyor relatively to the target 13.

Means 17 for coding for the required dose profile (on two sides) are located on the slave pallet 16.

Along the conveyor is arranged a dose profile encoder 18 coupled to profile reading arms.

Figure 3:
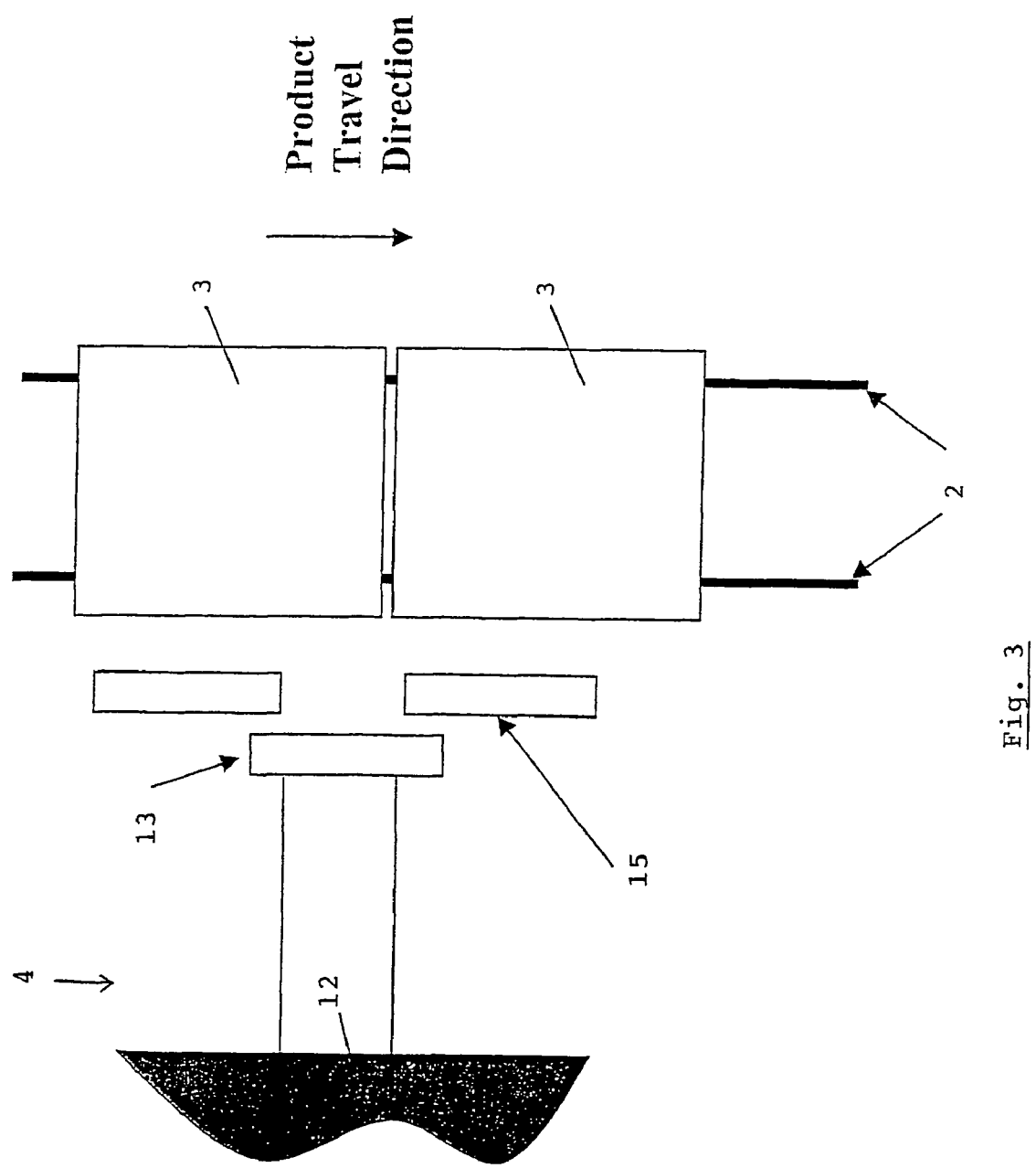
FIG. 3 represents a detailed top view of the apparatus according to the invention, showing the relative arrangement of the electron beam horn, the X-ray target, the collimators and the pallets conveyed.

A particular characteristic of the present invention is the presence of horizontal collimators 15 between the radiation source 4, more precisely the X-ray target 13 and the pallet 3 in the exposure portion 7 (pallet 3 in front of the X-ray target 13) as illustrated in FIG. 3. Said collimators 15 are used to define a constant aperture for the radiation beam (X-rays). This aperture is controlled by the control unit of the apparatus, namely according to the density of the products on the pallet 3, this aperture being smaller for higher density products. For products of low density, the aperture of these collimators is such large that one can consider that there are no collimators.

Table 1 gives aperture values of the collimators which can be advantageously used for different densities of products (two first columns), and the corresponding time exposure for a dose of 10 kGy and a beam power of 135 kW (column 4, treatment time). As shown in this table, for products of 0.8 g/cm³ density, an aperture of about 10 cm is preferred for the collimators, and the exposure time (treatment time) is preferably of about 224 minutes.

TABLE 1

| Density (g/cm3) | Aperture (cm) | α see equ. (1) | Treatment time |
|---|---|---|---|
| 0.2 | 60 | 0 | 26.5 |
| 0.4 | 45 | 0 | 35.7 |
| 0.6 | 18 | 0.6 | 99.1 |
| 0.8 | 10 | 0.7 | 224.2 |

The conditions for obtaining said results were the following:

the distance between two pallets 3 was equal to 10 cm;

the distance from the collimators 15 to the X-ray target 13 was constant and equal to 30 cm;

the distance from the X-ray target 13 to the centre of the product 3 was 112 cm.

Moreover, the collimators 15 were two steel plates but other types of collimators are also convenient in order to attenuate the irradiation beam relative to the product stack. For example, the collimators may also consist in a plurality of pipes filled with one or more fluids.

In all cases, the shape of the beam may be modified according to the properties (namely the density) of the product by modifying:

the aperture of the collimators (plates), the distance between the collimators and the radiation source (target), the angle between the collimators in the horizontal plane the filling of the pipes.

Another characteristic of the present invention is that the conveyor speed (horizontal translation speed) can vary as a function of the position of the pallet 3 on the exposure portion 7 of the conveyor circuit in front of the X-ray target 13. More precisely, the conveyor speed preferably follows the equation (1):

$$v(x)=1/(1-\alpha(\sin^2(\pi x/2d))) \quad (1)$$

wherein:

d is the half length of the pallet 3 in the conveyor direction x is the distance to the pallet centre beam along the beam direction α is the conveyor speed profile factor and depends on the density, the conveyor speed v(x) is therefore constant when α=0.

The modulation of the conveyor speed as well as the variation of the aperture of the collimators 15 both ensure an even irradiation dose of the pallet in the horizontal plane (direction perpendicular to the main axis of the target 13).

Table 1 column 3 gives examples of α values which can advantageously be used in function of the density of the product to be irradiated.

Figure 4:
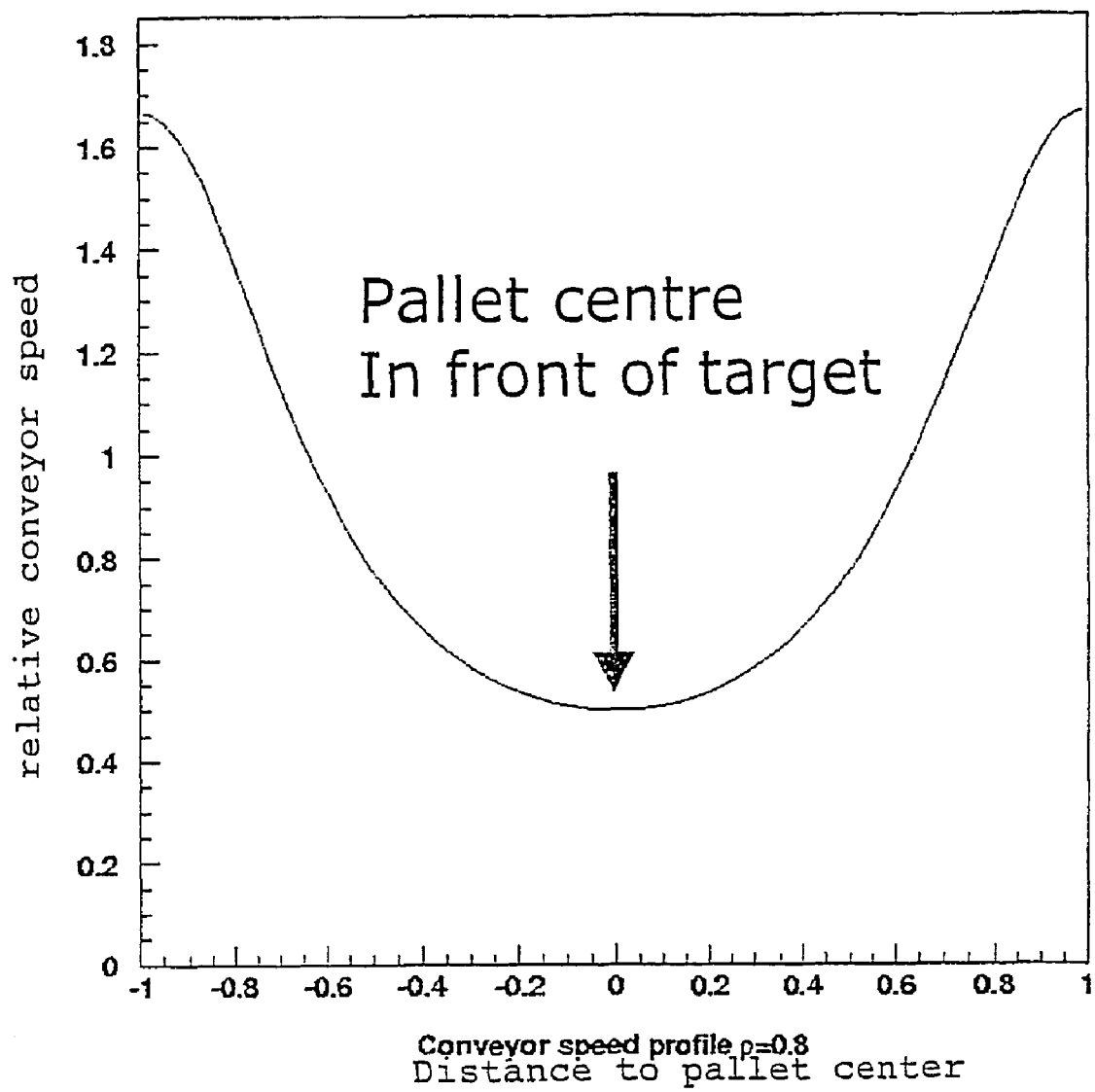
FIG. 4 represents the relative conveyor speed profile in function of the distance of the pallet centre to the beam axis in the present invention for a product density of $\rho=0.8$ g/cm$^3$.

FIG. 4 illustrates more precisely the relative conveyor speed profile as a function of the distance to the pallet centre (v(x)=f(x) as defined by equation (1)).

Preferably, the conveyor speed along the other portions 5, 6, 8, 9, 10 of the conveyor circuit 2 can also be varied in order to optimise the throughput and profitability of the apparatus (beam time).

As illustrated on FIG. 5a–5c, the apparatus according to the present invention presents very satisfying performances for irradiating products of low density as well as products of high density.

DESCRIPTION OF OTHER PREFERRED EMBODIMENTS

According to another preferred embodiment of the present invention, it is also possible to have an even radiation dose in the pallets in the horizontal plane by modulating the intensity of the radiation beam.

In this embodiment, specific means for modulating the intensity of the radiation beam are added, as compared to the embodiment disclosed hereabove and illustrated on FIGS. 2 and 3.

order to have an even radiation dose in the pallets in the vertical direction (i.e. in the main axis of target), one can use a radiation beam configured so as to overscan the pallets. The idea is to avoid that the top and bottom parts of the product get a smaller irradiation dose than the central part, the vertical beam scanning may be extended above and below the product itself. This means, in the case of X-rays, that the target height and scanning horn have to be larger than the maximum accepted pallet height. A value of 15 cm beyond the product limits has been proved to give satisfying results.

For this purpose, it is necessary to arrange additional small vertical collimators 20 (FIG. 2) in order to avoid any grazing incidence at the edges of the pallet. Preferably, the top vertical collimator may also be placed above the product, at a position in the beam direction corresponding to a fraction of the pallet size in that direction, rather than immediately downstream of the beam source. A particularly interesting value for this fraction is ⅓.

Alternatively said small vertical collimators 20 can be placed in front of the pallet 3.

An alternative consists in scanning the pallet 3 with a parallel non homogenous radiation beam.

It is also possible to obtain an even radiation zone in the vertical direction by modulating the vertical scanning speed of the photon source so that the top and bottom parts of the product are more than the central part. In the case of X-rays, the electron beam vertical scanning speed may for example be modulated by means of scanning magnets.

It should be noted that other embodiments could be envisaged in order to improve the performances of the proceeding.

For example, in order to overcome the degradation of the vertical uniformity of the irradiation due to the presence of the wood pallet supporting the product and have an optimum DUR, an asymmetric scanning beam width covering a longer area below the product than above may be generated. Keeping in mind that the optimum DUR depends also on both the density of the product and the source-product distance, one can consider however that for a density of the product equal to 0.1, the DUR is optimum for a vertical scan extending 15 cm above the product and 22 cm below.

Another problem comes from the vertical positioning which is critical as the vertical scanning speed varies as a function of the beam source position. As an illustration, a 10% DUR degradation may be observed for 5 cm misplacement. Moreover, the height of the wooden pallet supports varies between pallets.

To take this phenomenon into account, in another preferred embodiment, both the total height of product pallet and the height of the wooden pallet are measured prior to irradiation and the vertical scanning function is adapted in consequence.

In another embodiment, a solution concerns more particularly the treatment of products by batches of similar densities. Such treatment by batches ensures a maximised treatment efficiency, considering that the collimator aperture must be set differently for products of different densities and that moving the collimators is time consuming. However, time is lost when the batch which has completed its treatment exits the irradiation zone and another enters.

In this embodiment of the invention, this loss of time is minimised because the second batch enters the irradiation zone when the first batch is undergoing its last irradiation pass. More precisely, the beam may be stopped, or the photon source removed, when the last pallet of the first batch has been treated and moved away from the beam, or a sufficient gap must be left between the first pallet of the new batch and the last pallet of the first batch, such that the collimator aperture and other irradiation settings may be modified to those optimal for the new batch, in the time it takes for the first pallet to arrive in front of the beam source.

The invention claimed is:

1. Process for irradiation of a product having four vertical faces by a photon beam, said process comprising the following steps:
   introducing the product into an irradiation zone according to a horizontal translation movement,
   submitting said product to said photon beam, the photon beam having a vertical movement, the horizontal translation movement of the product and the vertical movement of the photon beam resulting in the irradiation of a vertical face of said product,
   moving said product out of the irradiation zone,
   giving a rotation of substantially 90° to said product using rotation means,
   reproducing said irradiation process until at least the four vertical faces of said product have been irradiated.

2. Process according to claim 1, wherein the rotation of the product is performed outside the irradiation zone.

3. Process according to claim 1, wherein the spread of the photon beam is limited.

4. Process according to claim 1, wherein the product is transferred in front of the photon beam in the irradiation zone according to a horizontal translation movement.

5. Process according to claim 1, wherein the speed of the product according to the horizontal translation movement is varied or modulated.

6. Process according to claim 5, wherein the horizontal translation speed of the product is lower when the center of the product is in front of the photon beam.

7. Process according to claim 1, wherein the speed of the vertical movement of the photon beam is modulated.

8. Process according to claim 7, wherein the speed of the vertical movement of the photon beam is lower when the center of the product is in front of the photon beam.

9. Process according to claim 7, wherein the speed of the vertical movement of the photon beam is performed by scanning elements.

10. Process according to claim 1, wherein the intensity of the photon beam is modulated.

11. Process according to claim 1, wherein the product consists of a first product and a second product, the second product being under the first product during a first irradiation process and the first product being under the second product during a further radiation process.

12. Process according to claim 1, wherein the product is loaded on a pallet and the total height of the product and the pallet is measured prior to irradiation in order to adapt the vertical scanning function.

13. Process according to claim 1, wherein the spread of the photon beam is adapted so as to allow an overscan of the product.

14. Process according to claim 1, wherein the scanning photon beam has an asymmetric width covering a longer area below the product than above.

15. Process according to claim 1, wherein the product is loaded on a pallet and the irradiation of the product is performed by batches of pallets loaded with products of similar densities.

16. Process according to claim 1, wherein the rotating means comprise a turntable or curved conveyor part defining a 90° turn.

17. The process according to claim 1, wherein said product is either of low density or high density.

18. Process for irradiation of a product having four vertical faces by a photon beam, consisting of an irradiation procedure comprising the following steps:
    introducing the product into an irradiation zone according to a horizontal translation movement,
    submitting said product to said photon beam, the photon beam having a vertical movement, the horizontal translation movement of the product and the vertical movement of the photon beam resulting in the irradiation of a vertical face of said product, wherein the spread of the photon beam is limited,
    moving said product out of the irradiation zone,
    reproducing said irradiation process until at least the four vertical faces of said product have been irradiated.

19. Process for irradiation of a product having four vertical faces by a photon beam, consisting of an irradiation procedure comprising the following steps:
    introducing the product into an irradiation zone according to a horizontal translation movement,
    submitting said product to said photon beam, the photon beam having a vertical movement, the horizontal translation movement of the product and the vertical movement of the photon beam resulting in the irradiation of a vertical face of said product, wherein the spread of the photon beam is limited,
    moving said product out of the irradiation zone,
    giving a rotation of substantially 90° to said product using rotation means, wherein the rotation of the product is performed outside the irradiation zone,
    reproducing said irradiation process until at least the four vertical faces of said product have been irradiated.

20. Apparatus for irradiating a product having four vertical faces by a photon beam, having
    1) A photon beam, 2) Means for conveying said product into and out of an irradiation zone,
    3) Means for translating said product inside the irradiation zone in front of the photon beam,
    4) Scanning means to vertically move said photon beam to scan a vertical face of the product,
    5) Means for rotating the product of an angle of substantially only 90° so that an adjacent vertical face of the product is irradiated, wherein the means for rotating are located outside of the irradiation zone.

21. Apparatus according to claim 20, further comprising homogenization means in order to limit the spread of the photon beam.

22. Apparatus according to claim 20, further comprising means for modulating the horizontal translation speed of the conveying means of the product in front of the photon beam.

23. Apparatus according to claim 20, further comprising means for modulating the vertical translation speed of the scanning means of the photon beam.

24. Apparatus according to claim 20, wherein the means for rotating consist of a turntable.

25. Apparatus according to claim 20, wherein the means for rotating consist of a curved conveyor part defining a 90° turn.

26. The apparatus according to claim 20 wherein said product is either of low density or high density.

27. Apparatus for irradiating a product having four vertical faces by a photon beam, having
    1) A photon beam,
    2) Means for conveying said product into and out of the irradiation zone,
    3) Means for translating said product inside the irradiation zone in front of the photon beam,
    4) Scanning means to vertically move said photon beam,
    5) A collimator to limit spread of the photon beam,
    6) A turntable for rotating the product of an angle of substantially 90°, wherein the turntable is located outside of the irradiation zone.

28. The apparatus according to claim 27, wherein said product is either of low density or high density.

* * * * *